(12) United States Patent
Taylor (10) Patent No.: US 6,629,451 B1
(45) Date of Patent: Oct. 7, 2003

(54) METHOD FOR DETERMINING THE RHEOLOGY OF A GELLED FLUID

(75) Inventor: Robert S. Taylor, Red Deer (CA)

(73) Assignee: Halliburton Energy Services, Inc., Duncan, OK (US)

( * ) Notice: Subject to any disclaimer, the term of this patent is extended or adjusted under 35 U.S.C. 154(b) by 0 days.

(21) Appl. No.: 10/123,745

(22) Filed: Apr. 16, 2002

(51) Int. Cl.$^7$ ............................................... G01N 11/14
(52) U.S. Cl. ..................................................... 73/54.28
(58) Field of Search ........................... 73/54.28, 54.29, 73/54.31, 54.32, 54.33, 54.34

(56) References Cited

U.S. PATENT DOCUMENTS

| | | | |
|---|---|---|---|
| 3,777,551 A | * 12/1973 | Weiss | ........................ 73/54.28 |
| 3,803,903 A | 4/1974 | Lin | |
| 3,875,791 A | 4/1975 | Fitzgerald et al. | |
| 4,077,251 A | 3/1978 | Winter | |
| 4,299,119 A | 11/1981 | Fitzgerald et al. | |
| 4,448,060 A | 5/1984 | Maruhnic | |
| 4,501,155 A | 2/1985 | Garritano | |
| 4,519,455 A | * 5/1985 | Holtmyer et al. | ........ 166/305.1 |
| 4,524,611 A | 6/1985 | Richon et al. | |
| 4,668,911 A | 5/1987 | Mueller et al. | |
| 4,760,734 A | 8/1988 | Maxwell | |
| 4,799,550 A | * 1/1989 | Harris et al. | ................. 166/300 |
| 4,878,377 A | 11/1989 | Abel | |
| 4,878,379 A | 11/1989 | Deer | |
| 4,887,671 A | * 12/1989 | Stevens, Jr. | .................. 166/308 |
| 5,365,777 A | 11/1994 | Layton | ...................... 73/54.28 |
| 5,987,970 A | 11/1999 | Ball | ......................... 73/54.28 |

* cited by examiner

Primary Examiner—Edward Lefkowitz
Assistant Examiner—Michael Cygan
(74) Attorney, Agent, or Firm—Robert A. Kent; William D. Hall (57) ABSTRACT

The current invention provides a method for determining the rheology of a mixture of gelled hydrocarbon and liquid carbon dioxide. The method of the current invention precludes the negative impact of the Weissenberg effect when determining the rheology of a non-Newtonian fluid. Additionally, the method of the current invention produces a homogenous mixture without generating the Weissenberg effect.

31 Claims, 3 Drawing Sheets

METHOD FOR DETERMINING THE RHEOLOGY OF A GELLED FLUID

BACKGROUND OF THE INVENTION

High viscosity gelled hydrocarbon fluids provide unique functional characteristics for a variety of applications. Although these fluids have a high viscosity, they are capable of breaking into thinner fluids under predetermined conditions. The oil industry uses these fluids in many day-to-day operations. Common applications include: fracturing subterranean formations penetrated by a well bore, forming gravel packs in a downhole environment, performing pigging operations in a pipeline and other applications requiring a viscous fluid. Although high in initial viscosity, these fluids are designed to subsequently breakdown into thinner fluids. The subsequent drop in fluid viscosity is necessary to permit production of hydrocarbons from the well.

Efficient formulation of gelled or viscosified hydrocarbon liquids requires prior knowledge of the viscosity of the liquid under the intended operating conditions. Due to difficulties in accurately determining rheology under downhole conditions, most well operators estimate the concentration of viscosity breaking agents necessary to lower, i.e. break, the viscosity of the gelled fluid using tests without the presence of liquid carbon dioxide. If the operator underestimates the concentration required to lower the viscosity, then production may be permanently impaired due to an unbroken gel. Absent the presence of viscosity breaking agents, oil gels will not break on their own accord over time. Accordingly, most operators add an excess of viscosity breaker to ensure an adequate drop in viscosity. However, excess use of viscosity breaker will prematurely degrade the viscosity of the fluid. This could result in a failure of the treatment to properly place the proppant in the fracture. Additionally, excess breaker usage unnecessarily increases costs. Clearly, the ability to accurately formulate the downhole fluid will greatly improve operational efficiency and reduce costs by eliminating over use of the viscosity breaking agents and other additives. Therefore, a method for determining the rheology of the gelled or viscosified hydrocarbon liquid under operational conditions will enhance the current state of the art.

The rotary viscometer is a tool commonly used to determine rheology of gelled hydrocarbon liquids. In general, a rotary viscometer includes a sample chamber, a rotary sleeve and a static bob coaxially positioned within the rotary sleeve. Depending upon the sample to be tested, the sample chamber may also include a heater.

When assessing the rheology of a fluid, the operator fills the sample chamber with sufficient fluid to cover a predetermined portion of the bob. Typically, a computer-controlled motor rotates the sleeve thereby shearing the fluid and transmitting torque via the fluid to the bob. The bob deflects due to the applied torque. Alternatively, one may measure the force required to maintain the bob in the stationary position or the power required to maintain the sleeve at a constant rotational speed. In general, the basic procedures for determining fluid rheology are well known in the art.

When using a standard sleeve and bob arrangement, measurement of the resulting angular displacement permits calculation of the shear stress experienced by the fluid. Additionally, the shear rate may be calculated by using the rotational speed and the known clearance distance between the sleeve and the bob. As known to those skilled in the art, apparent viscosity is determined by dividing the measured Shear Stress by the calculated Shear Rate. Preferably, standard sensors and instrumentation perform all such measurements and calculations automatically.

Most rotary viscometers are top driven units, i.e. the driving force for the sleeve is located above the sleeve. Therefore, current methods of using rotary viscometers require an air gap or void space separating the upper surface of the sample from the upper level of the sample chamber. The void space, filled with air or other undissolved gaseous material, acts as a buffer zone precluding entry of the sample into the bearings, drive system and sensing mechanism of the viscometer. Intrusion of the sample into these components is deleterious to the operation of the viscometer. At best, entry of the gelled fluid into the bearings increases drag and produces incorrect readings.

The risk of contamination increases when working with non-Newtonian fluids, as these fluids commonly exhibit the Weissenberg effect. The Weissenberg effect describes the tendency of a non-Newtonian fluid to climb up a rotating rod. When working with non-Newtonian fluids, the operator must take care not to overfill the sample chamber otherwise the non-Newtonian fluid will climb the shaft rotating the sleeve and contaminate the bearing and drive system. Therefore, it would be desirable to provide a method for determining the rheology of non-Newtonian fluids without the detrimental impact of the Weissenberg effect.

SUMMARY OF THE INVENTION

The current invention provides a method for determining the rheology of a mixture of gelled hydrocarbon fluid and liquid carbon dioxide. The method utilizes a bottom driven rotary viscometer, also known as a rheometer. The rotary viscometer has a sample chamber for holding the fluid to be examined. The sample chamber includes a rotary sleeve driven from below. Positioned coaxially within the rotary sleeve is a static bob. The static bob is connected to a device for measuring torque applied to the bob. Preferably, the device also calculates the apparent viscosity of the fluid sample. The sample chamber includes multiple ports for adding fluids to the chamber. Additionally, the sample chamber may be pressurized to a pressure ranging from about 3 MPa to about 103 MPa and heated to about 205° C. In practice, the chamber is typically operated at temperatures between about 0° C. and 175° C. Typical operating pressures will range from about 17 MPa to about 103 MPa. To ensure a homogeneous mixture of gelled hydrocarbon fluid and liquid carbon dioxide, the sample chamber includes a means for mixing the fluids within the sample chamber. One means for mixing the fluids is the addition of fins to the external walls of the rotary sleeve. Alternatively, the rotary sleeve may have grooves machined into or otherwise incorporated into the outer surface thereof to promote mixing. Thus, rotation of the sleeve provides the means for mixing the fluids.

According to the method of the current invention, a sample chamber located in a bottom driven rotary viscometer is filled with gelled hydrocarbon and liquid carbon dioxide in a manner to substantially fill the sample chamber thereby eliminating substantially all undissolved gases from the interior of the sample chamber. Any gas remaining in the sample chamber is likely carbon dioxide. Subsequently, the liquid carbon dioxide and gelled hydrocarbon are mixed to form a homogenous mixture. The components of the mixture are placed under pressure and optionally heated. Once a homogenous mixture has been formed, a drive shaft or other suitable means rotates a sleeve positioned within the sample chamber. The drive shaft is located beneath the sleeve. Sleeve rotation shears the fluid mixture and transmits torque via the mixture to a bob positioned coaxially within the sleeve. Torque measurements are taken and used to determine the rheology of the mixture within the sample chamber.

The current invention also provides a method for determining the rheology of a mixture of gelled hydrocarbon and liquid carbon dioxide at temperatures lower than room temperature. According to the method of the current invention, a sample chamber located in a bottom driven rotary viscometer is filled with gelled hydrocarbon and liquid carbon dioxide in a manner to substantially eliminate all undissolved gases from the interior of the sample chamber. Subsequently, the liquid carbon dioxide and gelled hydrocarbon are mixed to form a homogenous mixture. Before, during or after the mixing, the components of the mixture are cooled and placed under pressure. Once a homogenous mixture has been formed, a drive shaft or other suitable means rotates a sleeve positioned within the sample chamber. The drive shaft is located beneath the sleeve. Rotation of the sleeve shears the fluid mixture and transmits torque via the mixture to a bob positioned coaxially within the sleeve. Torque measurements are taken and used to determine the rheology of the mixture within the sample chamber.

The current invention also provides a method for precluding the Weissenberg effect when measuring the rheology of non-Newtonian fluids with a rotary viscometer. The method comprises the steps of filling a sample chamber located within a bottom driven rotary viscometer with a non-Newtonian fluid. After the sample chamber has been filled to a point where substantially all undissolved gases have been eliminated from the sample chamber, a drive shaft or other suitable means rotates a sleeve positioned within the chamber. The drive shaft is located beneath the sleeve. As the sleeve rotates, the non-Newtonian fluid shears and transmits torque to a static bob positioned coaxially within the sleeve. Torque exerted on the bob is measured and used to determine the rheology of the non-Newtonian fluid.

DETAILED DESCRIPTION OF THE INVENTION

The methods of the current invention will be readily understood by those skilled in the art by referring to the drawings. In illustrating and describing the current invention, like or identical reference numerals are used to identify common or similar elements. The figures are not necessarily to scale and certain features and views of the figures may be shown exaggerated in scale or in schematic form in the interest of clarity and conciseness. As used herein, the terms gelled and viscosified are used interchangeably and refer to the increased apparent viscosity of a liquid due to a cross-linking agent. The processes and additives for gelling or viscosifying hydrocarbon liquids are well known in the art. The term rheology refers to the mathematical description of the fluid flow behavior derived by measurements of shear stress at calculated shear rates. Finally, the term non-Newtonian fluid includes mixtures having non-Newtonian rheological characteristics.

Figure 3:
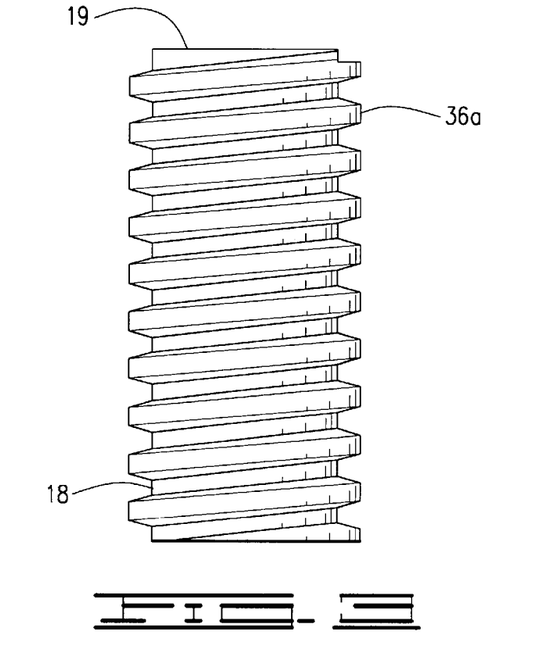
FIG. 3 is a side view of a rotatable sleeve with stirring fins.
Figure 4:
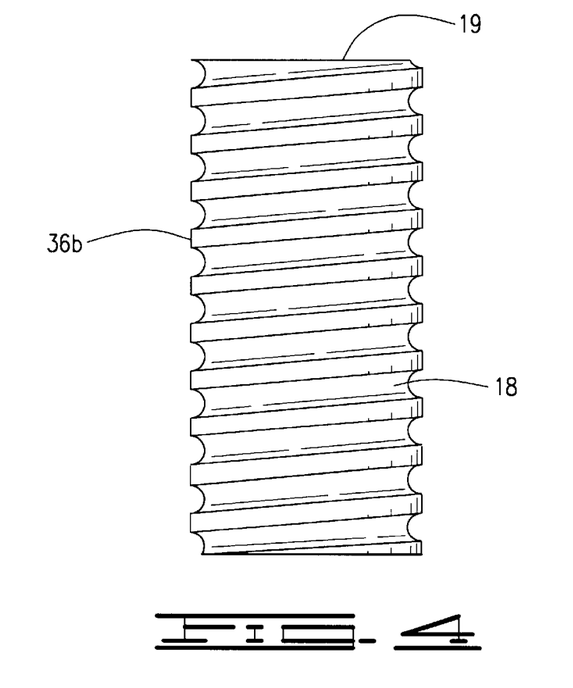
FIG. 4 is a side view of a rotatable sleeve with stirring grooves.

The current invention provides a method for measuring the rheology of gelled fluids. The method of the current invention utilizes a bottom driven rotary viscometer, preferably computer controlled, of the type shown in FIG. 1 and designated with the number 10. Rotary viscometer 10 includes a sample chamber 14, a rotatable sleeve 18 positioned within sample chamber 14 and a static bob 22 located coaxially within sleeve 18. Preferably, sleeve 18 also carries a means for mixing fluid within sample chamber 14. Examples of means for mixing the sample include helical fins 36a, as shown in FIG. 3, and spiral grooves 36b, as shown in FIG. 4. Fins 36a typically extend halfway into the annulus formed between sleeve 18 and sample chamber 14.

Figure 2:
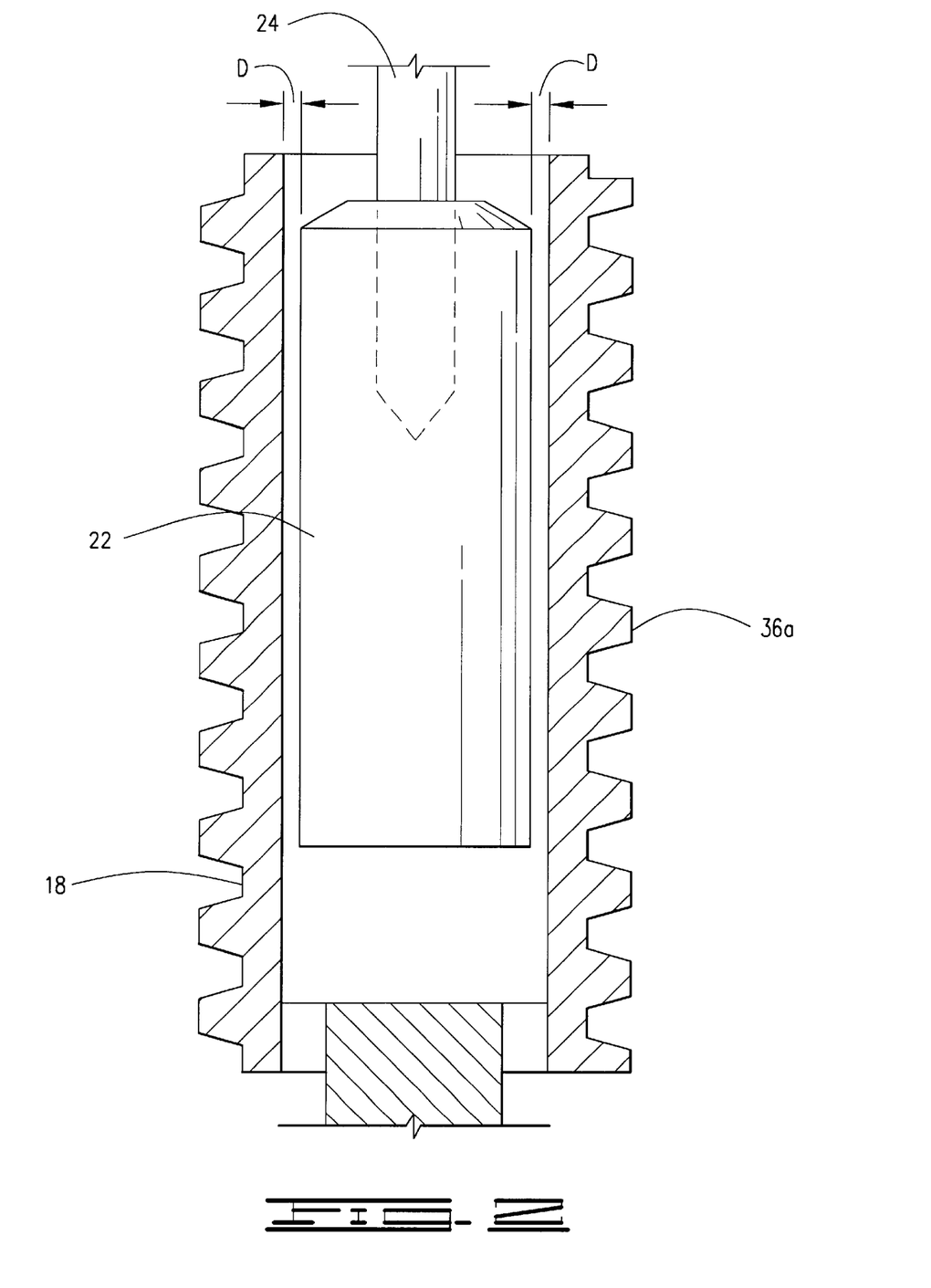
FIG. 2 is a side cut-away view showing a bob positioned within a rotatable sleeve.

As shown in FIG. 2, the annulus formed between bob 22 and sleeve 18 is designated as distance D. While D will vary depending upon the size of bob 22, D is a fixed known distance for each test. As known to those skilled in the art, the distance D is used to define the shear rate at a given rotational speed. In most rotary viscometers, shaft 24 connects static bob 22 to at least one spring, not shown, and a sensor, not shown. Each spring has a known spring constant. The sensor measures the degree of deflection experienced by bob 22. Preferably, the sensor communicates the deflection measurement to the computer or to a visual display, not shown. However, a spring/sensor configuration is only one of many means for measuring torque applied to static bob 22. Other arrangements may include electronic sensors or magnets attached to static bob 22 or shaft 24. Alternatively, the force required to rotate sleeve 18 at a constant speed may be measured and used to calculate fluid rheology. The actual mechanical means for obtaining a torque reading and/or rheology is not critical to the current invention.

Figure 1:
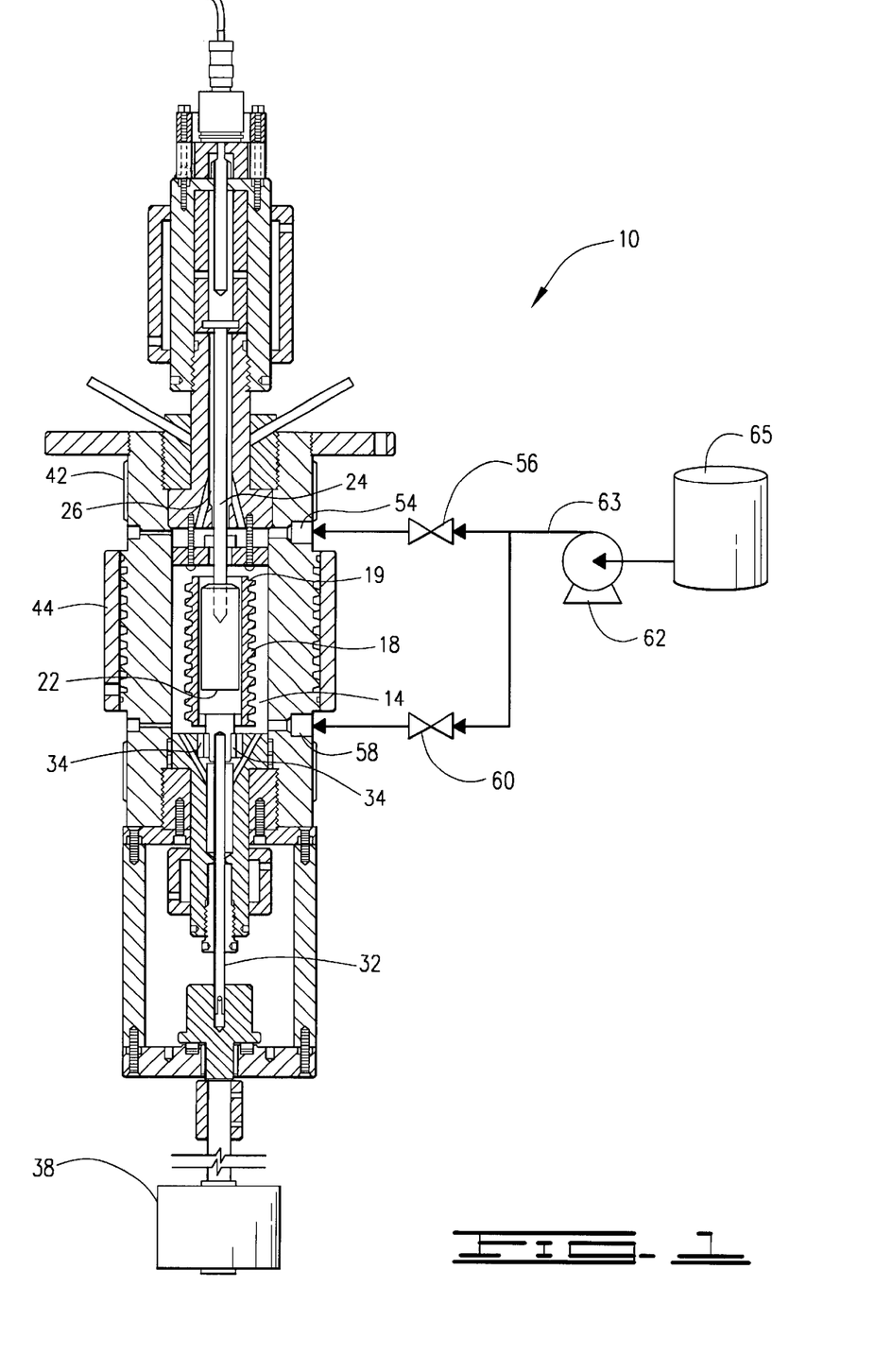
FIG. 1 is a side elevation of a bottom driven rotary viscometer suitable for performing the method of the current invention.

FIG. 1 depicts one embodiment of a bottom driven rotary viscometer. In this embodiment, the drive shaft 32 passes through a seal 34 positioned in the floor of sample chamber 14. Drive shaft 32 connects sleeve 18 to a drive mechanism 38 suitable for rotating sleeve 18. Preferably, drive mechanism 38 is a computer controlled stepper motor. However, other embodiments of drive mechanism 38 are contemplated. In this instance, drive shaft 32, coupled to the bottom of sleeve 18, provides the means to rotate sleeve 18. As shown in FIG. 1, drive shaft 32 applies rotational force to sleeve 18 at a point lower than upper edge 19. The actual location of drive mechanism 38 is not critical to the methods of the current invention provided that sleeve 18 is not driven by a shaft passing through the sample directly above sleeve 18.

Rotary viscometer 10 is fitted with at least one upper port 54 and at least one lower port 58. Ports 54 and 58 provide a means for adding and removing fluids from the interior of sample chamber 14. Valves 56 and 60 are fitted in ports 54 and 58, respectively, or in the lines leading to the ports. To simulate subsurface temperatures, rotary viscometer 10 utilizes heating means such as external heaters 42, controlled and monitored by at least one, preferably two thermocouples, not shown. The thermocouples are connected to at least one temperature controller, not shown. To help regulate the internal temperature, rotary viscometer 10 also includes a cooling means such as external cooling coils 44. Coils 44 are connected to a refrigerant or a cold water supply, not shown. Coils 44 also enable rheology analysis at lower than ambient temperatures. Preferably, the computer, through predetermined settings or by operator input, controls the temperature of the sample within sample chamber 14.

To simulate elevated pressures encountered downhole, a pump 62 connected to valve 56 and/or valve 60 by line 63 provides the means for pressurizing sample chamber 14. Line 63 includes a pressure transducer, not shown, for monitoring the pressure within sample chamber 14. Preferably, pump 62 is an air driven oil pump suitable for applying pressure to sample chamber 14. Pump 62 includes a reservoir 65 of ungelled hydrocarbon for pressurization of sample chamber 14. Pressure within sample chamber 14 may be monitored and controlled in several ways known to those skilled in the art. Preferably, the pressure transducer sends a signal to a digital display unit or the computer displaying pressure in values chosen by the operator. To avoid exceeding the maximum pressure rating of sample chamber 14, a rupture disk or pressure regulator, not shown, may be fitted to line 63. As with the temperature control, in the preferred embodiment the computer will control and monitor the pressure within the sample chamber based on predetermined settings or operator input.

An apparatus as described above and illustrated in FIG. 1 provides the means for practicing the current invention. The method of the current invention provides the ability to determine the rheology of a gelled fluid under conditions different from ambient temperature and pressure. Accordingly, the current invention provides methods for determining rheology under increased temperature and pressure as well as under temperature conditions lower than ambient. Additionally, the current invention provides a method for eliminating the Weissenberg effect when measuring the viscosity of a non-Newtonian fluid. The methods of the current invention will be described with continued reference to the drawings.

I. Rheology Determination Under Downhole Conditions

The current invention provides a method for testing mixtures of liquid carbon dioxide and gelled hydrocarbons under conditions that simulate the end-use environment of the fluid. Preferably, the mixtures are homogenous mixtures. A non-limiting list of commonly gelled hydrocarbons would include olefins, kerosene, diesel oil, gas oil, fuel oil and crude oil. According to the method of the current invention, the sample of gelled hydrocarbon fluid is introduced into sample chamber 14 through port 54 and/or port 58. Alternatively, the sample is poured into sample chamber 14 prior to assembling rotary viscometer 10. Depending on the nature of the fluid to be tested, the required volume of liquid carbon dioxide, up to 70% by volume, is added to sample chamber 14. Preferably, the liquid carbon dioxide enters sample chamber 14 through the annulus 26 surrounding static bob shaft 24 or other suitable entry port. The volume of the liquid carbon dioxide is sufficient to fill all remaining void spaces in sample chamber 14 and associated connected portions of bottom driven rotary viscometer 10. The addition of the liquid carbon dioxide typically raises the internal pressure of sample chamber 14 to the range of about 5.8 MPa to about 6.9 MPa (about 850 psi to about 1000 psi).

If the sample of gelled hydrocarbon is poured into sample chamber 14, then preferably gaseous carbon dioxide gas flows into sample chamber 14 during assembly of rotary viscometer 10. The flowing carbon dioxide gas displaces any air or other gases present in sample chamber 14. After assembly, liquid carbon dioxide is added as described above. The final volume of gelled hydrocarbon and liquid carbon dioxide in sample chamber 14 is sufficient to substantially fill sample chamber 14 thereby substantially eliminating all undissolved gases from sample chamber 14. Any unfilled volume (void space) remaining in sample chamber 14 will be less than the distance normally required to preclude the detrimental effects resulting from the Weisenburg effect in a top driven rotary viscometer and will likely be filled with carbon dioxide in liquid or gaseous form.

After filling the sample chamber, the method of the current invention provides the ability to determine fluid rheology over a range of elevated temperatures or at a single temperature including ambient temperature. The operator may manually input the desired temperature(s) or utilize a computer program designed to assess rheology at a single temperature point or multiple temperature points. According to the preferred embodiment of the current invention, once the computer receives the desired temperature input, the computer will control and monitor the temperature during the tests. When further heating is required, the computer activates external heaters 42 and thereby increases the temperature of the sample within sample chamber 14. External heaters 42 are connected to at least one and preferably two thermocouples, not shown. The thermocouples, in conjunction with a temperature controller, not shown, provide input data to the computer allowing it to maintain the desired temperature. When testing fluids used in a downhole environment, typical test temperatures may range between about 20° to about 175° C.

Downhole simulation typically requires application of increased pressure to sample chamber 14. The required pressure is established at the beginning of the analysis with the necessary phase ratios of gelled fluid to liquid $CO_2$. The method of the current invention provides for rheology determinations at pressures from about 3 MPa to about 103 MPa. For fluids used in a downhole environment, common testing pressures will be in the range of about 17 MPa to about 103 MPa. Final pressurization takes place after filling sample chamber 14. Preferably, final pressurization is achieved by pumping a predetermined volume of ungelled hydrocarbon from reservoir 65, through line 63, to valves 56 and/or 60 and into sample chamber 14. The predetermined volume of ungelled hydrocarbon is calculated by first determining the total volume of all void spaces associated with the bottom driven rotary viscometer accessible to the liquid carbon dioxide including sample chamber 14, then determining the desired ratio of gelled hydrocarbon to liquid carbon dioxide. Once the final volume of gelled hydrocarbon is known, a portion of the fluid to be gelled is stored in reservoir 65 in the ungelled state. The portion withheld is subsequently forced into sample chamber 14 by pump 62. The addition of the ungelled fluid to the filled and otherwise sealed sample chamber 14 raises the pressure within sample chamber 14 to the desired range. The ungelled fluid subsequently becomes part of the gel and liquid carbon dioxide mixture.

Prior to determining fluid rheology, the current invention provides a homogenous mixture in sample chamber 14 by rotating sleeve 18 by means of a drive shaft 32 or other suitable means located beneath sleeve 18. Preferably, sleeve 18 has a set of external fins 36a as shown in FIGS. 2 and 3 or a set of machined spiral grooves 36b as shown in FIG. 4. Either feature, as well as other configurations, will adequately mix the sample to produce a homogeneous mixture. Mixing the sample may take place prior to, during or after establishing the desired temperature and/or pressure within sample chamber 14. The rotational speed of sleeve 18 necessary to produce a homogenous mixture will vary depending upon the nature of the fluid as well as the temperature and pressure within sample chamber 14. If necessary to achieve thorough mixing, sleeve 18 may be rotated at speeds up to about 105 radian/sec (about 1000 rpm).

Following generation of the homogenous mixture, sleeve 18 is rotated from below by drive shaft 32 or an equivalent. The rotational speed must be sufficient to shear the fluid and transmit torque to static bob 22. The requisite rotational speed will vary depending upon the size of static bob 22, the nature of the gelled or viscosified fluid and test conditions such as temperature and pressure. In general, one skilled in the art will be able to readily determine the appropriate rotational speeds necessary to generate accurate rheology results. Typically, fluid rheology assessment requires at least two shear stress measurements at a minimum of two different shear rates. Variations in shear rate are obtained by varying the rotational speed of sleeve 18.

The torque applied to static bob 22 produces a measurable deflection of static bob 22. The deflection registers on a gauge, sensor or other similar output device, not shown, as either a torque reading or a viscosity measurement. If a torque reading is generated, then fluid rheology is calculated based on knowledge of static bob's 22 resistance to deflection. Preferably, a sensor and computer suitable for automatically calculating apparent fluid viscosity are connected to the deflection sensing device.

II. Rheology Determination Under Reduced Temperatures

The current invention also permits rheology analysis at reduced temperatures. The temperature controls suitable for high temperature analysis also provide the means for low temperature analysis. Specifically, the computer monitors sample temperature by means of at least one and preferably two thermocouples, not shown. In response to input from either the operator or the thermocouple(s), the computer controls the flow of refrigerant through coils 44 and/or activates heaters 42 to maintain temperature in the desired range. The method of the current invention provides for cooling of the sample to temperatures ranging from about 0° to about 20° C.

According to this method, the sample of gelled hydrocarbon fluid is introduced into sample chamber 14 either through port 54 and/or port 58. Alternatively, the sample is poured into sample chamber 14 prior to assembling rotary viscometer 10. A non-limiting list of commonly gelled hydrocarbons would include olefins, kerosene, diesel oil, gas oil, fuel oil and crude oil. Depending on the nature of the fluid to be tested, a quantity of liquid carbon dioxide, up to 70% by volume, is added to sample chamber 14. Preferably, the liquid carbon dioxide enters sample chamber 14 through annulus 26 surrounding bob shaft 26. The volume of the liquid carbon dioxide is sufficient to fill all remaining void spaces in sample chamber 14 and associated connected portions of bottom driven rotary viscometer 10. The addition of the liquid carbon dioxide typically raises the internal pressure of sample chamber 14 to the range of about 5.8 MPa to about 6.9 MPa (about 850 psi to about 1000 psi).

If the sample of gelled hydrocarbon is poured into sample chamber 14, then preferably gaseous carbon dioxide flows into sample chamber 14 during assembly of rotary viscometer 10. The flowing carbon dioxide gas displaces any air or other gases present in sample chamber 14. After assembly, liquid carbon dioxide is added as described in the prior section. The final volume of gelled hydrocarbon and liquid carbon dioxide substantially fills sample chamber 14 thereby eliminating substantially all undissolved gases from sample chamber 14. Any unfilled volume (void space) remaining in sample chamber 14 will be less than the distance normally required to preclude the detrimental effects resulting from the Weissenberg effect in a top driven rotary viscometer and will likely be filled with carbon dioxide in liquid or gaseous form.

After filling the sample chamber, the method of the current invention provides the ability to determine fluid rheology over a range of temperatures lower than room temperature or at a single temperature. The operator may manually input the desired temperature(s) through the computer or establish a computer program for rheology determinations at a single temperature point or multiple temperature points. In either case once the computer receives the desired temperature input, it will control and monitor the temperature setting during the tests. The method reduces sample temperature by passing a refrigerant through cooling coils 44. Suitable refrigerants include but are not limited to: cold water, ethylene glycol or liquid nitrogen. The thermocouple in conjunction with the temperature controller and external heaters 42, provide input data to the computer and/or operator allowing for maintenance and control of the desired temperature. If necessary to preclude excess cooling, external heaters 42 may be activated to maintain the desired temperature range.

The method also provides for testing of the chilled sample at increased pressures in the same manner as described above in the high temperature testing method. The required pressure is established at the beginning of the analysis with the necessary phase ratios of gelled fluid to liquid carbon dioxide. The method of the current invention provides for rheology determinations at pressures from about 3 MPa to about 103 MPa. For fluids used in a downhole environment, common testing pressures will be in the range of about 17 MPa to about 103 MPa. Final pressurization takes place after filling sample chamber 14. Preferably, final pressurization is achieved by pumping a predetermined volume of ungelled hydrocarbon from reservoir 65, through line 63, to valves 56 and/or 60 and into sample chamber 14. The predetermined volume of ungelled hydrocarbon is calculated by first determining the total volume of sample chamber 14 including all connecting void spaces, then determining the desired ratio of gelled hydrocarbon to liquid carbon dioxide. Once the final volume of gelled hydrocarbon is known, then a portion of the fluid to be gelled is stored in reservoir 65 in the ungelled state. The portion withheld is subsequently forced into sample chamber 14 by pump 62. The addition of the ungelled fluid to the filled and otherwise sealed sample chamber 14 raises the pressure to the desired range. The ungelled fluid subsequently becomes part of the gel and liquid carbon dioxide mixture.

Prior to determining fluid rheology, the current invention provides a homogenous mixture in sample chamber 14 by rotating sleeve 18 by a means such as drive shaft 32 or other suitable device coupled to drive mechanism 38. Preferably, sleeve 18 has a set of external fins 36a as shown in FIGS. 2 and 3 or a set of machined spiral grooves 36b as shown in FIG. 4. Either feature, as well as other configurations, will adequately mix the sample to produce a homogeneous mixture. Sample mixing may take place prior to, during or after establishing the desired temperature and/or pressure within sample chamber 14. The rotational speed of sleeve 18 necessary to produce a homogenous mixture will vary depending upon the nature of the fluid as well as the temperature and pressure within sample chamber 14. If necessary to achieve thorough mixing, sleeve 18 may be rotated at speeds up to about 105 radian/sec (about 1000 rpm).

Following generation of the homogenous mixture, sleeve 18 is rotated from below by drive shaft 32 or an equivalent. The rotational speed must be sufficient to shear the fluid and transmit torque to static bob 22. Rotational speed will vary depending upon the size of static bob 22, the nature of the gelled or viscosified fluid and test conditions such as temperature and pressure. In general, one skilled in the art will be able to readily determine the appropriate rotational speeds necessary to generate accurate rheological assessments. Typically, fluid rheology assessment requires at least two shear stress measurements at a minimum of two different shear rates. Variations in shear rate are obtained by varying the rotational speed of sleeve 18.

The torque applied to static bob 22 produces a measurable deflection of static bob 22. The deflection registers on a gauge, sensor or other similar output device, not shown, as either a torque reading or a viscosity measurement. If a torque reading is generated, then fluid rheology is calculated based on knowledge of static bob's 22 resistance to deflection. Preferably, a sensor and computer suitable for automatically calculating apparent fluid viscosity are connected to the deflection sensing device.

III. Elimination of the Weissenberg Effect

The current invention also provides a method for eliminating the Weissenberg effect when determining the rheology of a non-Newtonian fluid, for example a mixture of gelled hydrocarbon and liquid carbon dioxide. Since this method eliminates the Weissenberg effect, the void space normally required in rotary viscometers is not required. After filling sample chamber 14 to the desired level, the chamber may be optionally heated or cooled as described above. Further, sample chamber 14 may be pressurized in the manner described above. Preferably, the quantity of sample substantially fills sample chamber 14 and displaces substantially all air or undissolved gas from within sample chamber 14. Thus, a void space is not required in the method of the current invention.

If the non-Newtonian fluid is a mixture of different components, then a homogenous mixture must be generated in order to yield accurate rheological assessments. The homogenous mixture is achieved by rotating sleeve 18 from below by means of drive shaft 32 or its equivalent. Sleeve 18 carries mixing means such as fins 36a in a helical configuration or spiral grooves 36b. Thus, rotation of sleeve 18 from below provides adequate mixing of solutions to produce a homogenous mixture. Typically, the rotational speed of sleeve 18 necessary to mix the fluid will be greater than the rotational speed normally used for rheology determination. If necessary to achieve thorough mixing, sleeve 18 may be rotated at speeds up to about 105 radian/sec (about 1000 rpm).

Following generation of the homogenous mixture, drive mechanism 38 rotates sleeve 18 at a speed appropriate to generate the shear required for rheology determination. The requisite rotational speed will vary depending upon the size of static bob 22, the nature of the non-Newtonian fluid and test conditions such as temperature and pressure. In general, one skilled in the art will be able to readily determine the appropriate rotational speeds necessary to generate accurate rheological assessment. Typically, fluid rheology assessment requires at least two shear stress measurements at a minimum of two different shear rates. Variations in shear rate are obtained by varying the rotational speed of sleeve 18.

Rotating the sleeve shears the fluid mixture and transmits torque via the mixture to static bob 22. The torque experienced by static bob 22 results in a deflection of static bob 22. The deflection registers on a gauge, sensor or other similar output device, not shown, as either a torque reading or a viscosity measurement. If a torque reading is generated, then the rheology of the fluid is calculated based on knowledge of the resistance of static bob 22 to deflection. Preferably, a sensor and computer suitable for automatically determining fluid rheology are connected to the deflection sensing device.

The following examples are provided merely to aid in the understanding of the current invention and should not be interpreted as limiting the scope of the attached claims. The following examples were performed on a bottom driven rotary viscometer using a sleeve having a radius of 1.842 cm and a bob having a radius of 1.724 cm and a length of 7.6 cm. The non-Newtonian fluid used in each of the following examples was #2 diesel viscosified with a phosphate ester/ferric iron complex and the ungelled fluid used in each example was #2 diesel oil.

EXAMPLE 1

Elimination of Weissenberg Effect

To demonstrate the elimination of the Weissenberg effect, the sample chamber was filled with gelled #2 diesel to a level sufficient to cover the bob. The cell was pressurized with ungelled #2 diesel liquid $CO_2$ was omitted from this test. Since this example is intended to demonstrate the elimination of the Weissenberg effect, omission of liquid $CO_2$ does not impact the results.

The sample chamber was initially pressurized to about 16.95 MPa. Over the course of the three-hour test, the internal pressure was maintained between 17.96 MPa and 15.90 MPa with an average pressure of 17.1 MPa. Following pressurization, the sleeve was initially rotated at 1.57 radian/sec (15 rpm) increasing to 10.5 radian/sec (100 rpm) and decreasing again to 1.57 radian/sec (15 rpm). Subsequently, rotational speed was maintained at 1.57 radian/sec (15 rpm) for the duration of the test. Test cell temperature was maintained at 17° C. for the duration of the test. Although the indicated as a constant 17° C. some temperature variation likely occurred resulting in the variation of pressure during the test.

Viscosity readings taken during the three-hour test demonstrated good shear stress response to shear rate versus time. The shear stress response to shear rate demonstrates satisfactory functioning of the rotary viscometer and lack of gelled hydrocarbon in the bearings. Additionally, the bearings were physically examined and found to be free of gelled hydrocarbon. Thus, the method of the current invention avoids the detrimental results of the Weissenberg effect while producing satisfactory rheological readings.

EXAMPLE 2

Mixing with Helical Fins

This example demonstrates the ability to eliminate the Weissenberg effect while using a bottom driven sleeve to produce a homogenous mixture of gelled oil and an ungelled liquid. Mounted on the exterior of the sleeve are helical fins. The fins extend halfway into the annular space between the sleeve and the interior wall of the test cell. As in example 1, liquid $CO_2$ has been omitted from this test. Since this test is designed to demonstrate the ability of the helical fins to generate a homogenous mixture, the omission of liquid $CO_2$ will not impact the results. However, due to the higher viscosity of the ungelled oil as compared to liquid $CO_2$, the time necessary to produce a homogenous mixture of gelled and ungelled oil will be greater than time necessary to yield a homogenous mixture of gelled oil and liquid $CO_2$.

The test cell was half filled with gelled oil and the remainder of the cell filled with ungelled oil. The cell was pressurized to an initial pressure of 17.02 MPa (2468 psi). During the test, cell pressure was maintained between 16.87 MPa and 14.22 MPa (2447 psi and 2063 psi) and the cell temperature was maintained at 19° to 20° C. To produce the desired homogenous mixture, the sleeve was initially rotated at 62.83 radian/sec (600 rpm) for five minutes and then at 10.5 radian/sec (100 rpm) for three hours. As the sleeve rotated, a rotational flow pattern was observed with the fluid rising near the cell wall and falling near the center of the cell. The fluid did not "climb" the shaft supporting the static bob.

As shown by Table 1 below, apparent fluid viscosity rapidly decreased over the first 30 to 40 minutes of mixing. The subsequent stabilization of fluid viscosity indicates the presence of a homogenous mixture. The continued gradual loss of viscosity shown in the table is the expected result of shear stress on fluids of this nature. Rotation of the sleeve at 10.5 radian/sec (100 rpm) was maintained for an additional 12 hours. Upon completion of the test, the bearings were examined and were found to be free of gelled fluid.

TABLE 1

Viscosity vs. Time

Clearly, the methods of the current invention provide a high level of flexibility when determining the rheology of gelled and viscosified fluids under conditions of increased pressure and elevated or reduced temperature. Although optional, the use of a computer to control the rotary viscometer will allow the operator to establish multiple testing points at a variety of temperatures and shear rates. Since the method of the current invention eliminates the need for a void space or air gap, all of these tests can be performed on a single sample without stopping to clean the instrument.

While the present invention has been described in detail with reference to FIGS. 1–4 and the examples, other embodiments of the device and methods for performing the current invention will be apparent to those skilled in the art. Thus, the foregoing specification is considered exemplary with the true scope and spirit of the invention being indicated by the following claims.

I claim:

1. A method for determining the rheology of a mixture of gelled hydrocarbon and liquid carbon dioxide comprising the steps of:

a) filling a sample chamber located in a rotary viscometer with a gelled hydrocarbon and liquid carbon dioxide thereby substantially eliminating all undissolved gas from said sample chamber;

b) mixing said liquid carbon dioxide and said gelled hydrocarbon to form a homogenous mixture;

c) rotating a sleeve positioned within said sample chamber thereby shearing said mixture;

d) determining the shear rate experienced by said mixture;

e) increasing the pressure within said sample chamber by adding additional ungelled hydrocarbon prior to determining the rheology of said mixture; and g) determining the rheology of said mixture.

2. The method of claim 1, further comprising the step of heating said mixture prior to determining the rheology of said mixture.

3. The method of claim 3, wherein said mixture is heated to a temperature between about 20° C. to about 205° C.

4. The method of claim 1, wherein said step of applying pressure raises the pressure of said mixture to a final pressure in the range of about 3 MPa to about 103 MPa.

5. The method of claim 1, further comprising the step of determining the shear stress exerted on said mixture.

6. The method of claim 5, further comprising the step of rotating said sleeve at minimum of two different rotational velocities and determining the shear stress exerted on said mixture at each rotational velocity.

7. The method of claim 1, further comprising the step of measuring the torque exerted on a bob coaxially positioned within said sleeve prior to the step of determining the rheology of said mixture.

8. The method of claim 1, wherein said gelled hydrocarbon comprises a hydrocarbon selected from the group consisting of olefins, kerosene, diesel oil, gas oil, fuel oil, crude oil and mixtures thereof.

9. The method of claim 1, wherein step b) is performed by rotating a sleeve positioned within said sample chamber at a rotational speed of up to about 105 radian/sec.

10. The method of claim 1, wherein said mixture comprises up to about 70% liquid carbon dioxide by volume.

11. The method of claim 1, step c) wherein said sleeve is rotated by a drive shaft connect to the lower portion of said sleeve.

12. A method for determining the rheology of a gelled hydrocarbon fluid comprising the steps of:

a) filling a sample chamber located in a rotary viscometer by filling said sample chamber with a gelled hydrocarbon and liquid carbon dioxide thereby substantially eliminating all undissolved gas from said sample chamber;

b) mixing said liquid carbon dioxide and said gelled hydrocarbon to form a mixture;

c) cooling said mixture;

d) rotating a sleeve positioned within said sample chamber thereby shearing said mixture; and, e) determining the rheology of said mixture.

13. The method of claim 12, wherein said step of cooling lowers the temperature of said mixture to the range of about 0° C. to about 20° C.

14. The method of claim 12, further comprising the step of increasing the pressure within said sample chamber prior to determining the rheology of said mixture.

15. The method of claim 14, wherein said step of increasing the pressure within said sample chamber is achieved by adding additional gelled hydrocarbon through at least one port located in the upper half of said sample chamber.

16. The method of claim 15, wherein said step of applying pressure raises the pressure of said mixture to a final pressure in the range of about 3 MPa to about 103 MPa.

17. The method of claim 12, further comprising the step of determining the shear stress exerted by said mixture.

18. The method of claim 17, further comprising the step of rotating said sleeve at minimum of two different rotational velocities and determining the shear stress exerted on said mixture at each rotational velocity.

19. The method of claim 12, further comprising the step of measuring the torque exerted on a bob coaxially positioned within said sleeve prior to the step of determining the rheology of said mixture.

20. The method of claim 12, wherein said gelled hydrocarbon comprises a hydrocarbon selected from the group consisting of olefins, kerosene, diesel oil, gas oil, fuel oil, crude oil and mixtures thereof.

21. The method of claim 12, wherein said step b) is performed by rotating a sleeve positioned within said sample chamber at a rotational speed of up to about 105 radian/sec.

22. The method of claim 12, wherein said mixture comprises up to about 70% liquid carbon dioxide by volume.

23. The method of claim 12, step d) wherein said sleeve is rotated by a drive shaft connect to the lower portion of said sleeve.

24. A method for precluding the Weissenberg effect when determining the rheology of non-Newtonian fluids using a rotary viscometer comprising the steps of:

a) filling a sample chamber with a non-Newtonian gelled fluid thereby eliminating substantially all undissolved gases from said sample chamber;

b) pressurizing the sample chamber by adding additional ungelled fluid to the non-Newtonian gelled fluid, said fluid being the same as used in preparing the gelled fluid:

c) rotating a sleeve positioned within said sample chamber by means of a drive shaft connect to the lower portion of said sleeve thereby shearing said non-Newtonian fluid and thereby eliminating the Weissenberg effect; and, d) determining the rheology of said non-Newtonian fluid.

25. The method of claim 24, additionally comprising the step of measuring the torque applied to a bob coaxially positioned within said sleeve prior to the step of determining the rheology of said mixture.

26. The method of claim 24, wherein said non-Newtonian fluid comprises a mixture of gelled hydrocarbons and liquid carbon dioxide.

27. The method of claim 26, further comprising the step of mixing said mixture of gelled hydrocarbons and liquid carbon dioxide to provide a homogenous mixture prior to the step of measuring the torque applied to the bob.

28. The method of a claim 27, wherein said step of mixing is carried out by rotating said sleeve at a rotational speed of up to about 105 radian/sec.

29. The method of claim 24, prior to step c), further comprising the step of determining the shear stress exerted on said non-Newtonian fluid.

30. The method of claim 29, further comprising the step of rotating said sleeve at minimum of two different rotational velocities and determining the shear stress exerted on said non-Newtonian at each rotational velocity.

31. The method of claim 24, further comprising the step of measuring the torque exerted on a bob coaxially positioned within said sleeve prior to the step of determining the rheology of said non-Newtonian fluid.

* * * * *